United States Patent
McCarthy et al.

(10) Patent No.: US 6,452,285 B1
(45) Date of Patent: Sep. 17, 2002

(54) FABRICATION OF STANDARD DEFECTS IN CONTACTS

(75) Inventors: Michael McCarthy, Round Rock; David Cooper, Austin, both of TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 46 days.

(21) Appl. No.: 09/690,157

(22) Filed: Oct. 17, 2000

(51) Int. Cl.[7] .......................... H01L 29/78; H01L 33/00
(52) U.S. Cl. ........................ 257/797; 257/652
(58) Field of Search .................. 257/798, 797, 257/652

(56) References Cited

U.S. PATENT DOCUMENTS

| | | | |
|---|---|---|---|
| 4,473,795 A | * | 9/1984 | Wood |
| 5,004,340 A | * | 4/1991 | Tullis et al. |
| 5,508,800 A | * | 4/1996 | Miyashita |
| 5,691,812 A | * | 11/1997 | Bates et al. |
| 5,815,275 A | * | 9/1998 | Svetkoff et al. |
| 6,274,396 B1 | * | 8/2001 | Funsten |

OTHER PUBLICATIONS

Stanley Wolf and Richard N. Tauber; Silicon Processing for the VLSI Era, vol. 2—Process Integration; pp. 87–110; 1990.

* cited by examiner

Primary Examiner—Stephen D. Meier
(74) Attorney, Agent, or Firm—Timothy M. Honeycutt

(57) ABSTRACT

Various circuit devices for contact defect inspection and methods of fabrication and use thereof are provided. In one aspect, a circuit device is provided that includes a substrate and an insulating film positioned on the substrate that has a plurality of openings therein. A plurality of members is provided. Each of the plurality of members is positioned in one of the plurality of openings and has known dimensions. The plurality of members provide a known set of defects in the plurality of openings to facilitate inspection of the plurality of openings. The circuit device may be used to accurately calibrate inspection tools to detect contact defects.

17 Claims, 3 Drawing Sheets

US 6,452,285 B1

FABRICATION OF STANDARD DEFECTS IN CONTACTS

BACKGROUND OF THE INVENTION

1. Field of the Invention

This invention relates generally to semiconductor processing, and more particularly to a circuit device incorporating standardized contact defects and to methods of fabricating the same.

2. Description of the Related Art

Large scale integrated circuits now routinely contain millions of individual transistors and other electronic components. Most of the interconnections for the numerous individual components are provided via one or more metallization layers that serve as global interconnect levels. Each metallization layer is ordinarily deposited on the substrate of the integrated circuit as a single continuous layer that is thereafter patterned lithographically and etched to remove metal from areas where metal lines are not required.

In addition to the one or more metallization layers, modern integrated circuits also incorporate numerous routing-restricted interconnect levels commonly known as local interconnects and contacts. Local interconnects and contacts are used for short metallization runs such as those that locally interconnect gates and drains in NMOS and CMOS circuits and those that connect a given metallization layer to a particular structure in the integrated circuit.

A method frequently employed to form contact structures involves a damascene process in which the substrate containing the integrated circuit is coated with a layer of dielectric material that is lithographically patterned and etched to form contacts or vias in the dielectric layer where the contact structures will be formed. Thereafter, the contact material, or materials if a laminate structure is desired, is deposited over the dielectric layer. The goal of the deposition process is to fill the vias as completely as possible. Finally, a planarization process is performed to remove the excess conducting material from the dielectric layer and leave only the filled vias.

Accurate and reliable defect inspection is vital to successful semiconductor fabrication. Microelectronic circuit structures, such as contact structures, may be highly sensitive to contamination by particulates introduced by various semiconductor processing tools and to the various deleterious effects associated with unwanted residual films left over after semiconductor processing steps or unanticipated poor process control. Examples of process irregularities that contact formation may present are legion, and include such things as partially cleared contacts, partially or fully closed contacts, and scumming.

Currently, inspection for contact defects is performed with various types of scanning tools. Some of these employ optical scanning, while others utilize laser scanning. Many conventional contact defect scanning techniques utilize die-to-die comparison, although die-to-database comparing is also sometimes used.

A difficulty associated with conventional contact defect scanning is tool calibration. In order for a given inspection tool to be able to accurately identify and characterize contact defects, the inspection tool must be instructed or otherwise programmed to scan in certain locations on the wafer for certain features that are indicative of a defect. For contact defect inspection, the task of tool calibration has proved to be difficult. The problem stems from the fact that both the contacts and the defects come in a variety of geometries. This lack of a standard geometry from which to calibrate the inspection tool means that tool calibration for parameters such as optimum depth of focus may involve some degree of experimentation. Accordingly, where the contact formation process is changed, the trial and error method of calibration must be repeated.

The present invention is directed to overcoming or reducing the effects of one or more of the foregoing disadvantages.

SUMMARY OF THE INVENTION

In accordance with one aspect of the present invention, a circuit device is provided that includes a substrate and an insulating film positioned on the substrate that has a plurality of openings therein. A plurality of members is provided. Each of the plurality of members is positioned in one of the plurality of openings and has known dimensions. The plurality of members provide a known set of defects in the plurality of openings to facilitate inspection of the plurality of openings.

In accordance with another aspect of the present invention, a test circuit device is provided that includes a substrate and an insulating film positioned on the substrate that has a plurality of openings therein. A plurality of metal pegs is provided. Each of the plurality of metal pegs is positioned in one of the plurality of openings and has known dimensions. The plurality of metal pegs provide a known set of defects in the plurality of openings to facilitate inspection of the plurality of openings.

In accordance with another aspect of the present invention, a method of fabricating a circuit device on a substrate is provided that includes forming a plurality of members on the substrate, each with known dimensions and an upper surface. An insulating film is formed over the members and openings in the insulating film are formed to expose at least the upper surfaces of the plurality of members.

In accordance with another aspect of the present invention, a method of inspecting a first plurality of contacts in an insulating film for defects utilizing an inspection tool is provided. The method includes forming a plurality of members in a second plurality of contacts. The plurality of members have known dimensions. The inspection tool is calibrated using the plurality of members as a known set of defects in the second plurality of contacts. Thereafter, the first plurality of contacts is inspected using the calibrated inspection tool.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
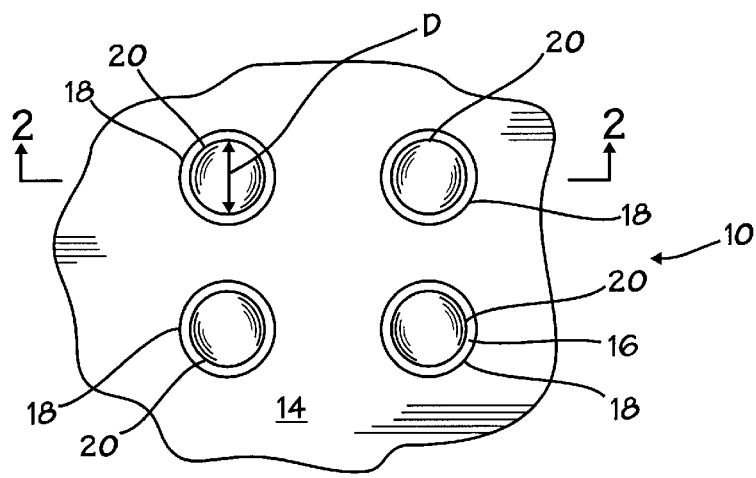
FIG. 1 is a plan view of an exemplary embodiment of a circuit device that is suitable for calibrating a semiconductor workpiece inspection tool or substrate in accordance with the present invention.
Figure 2:
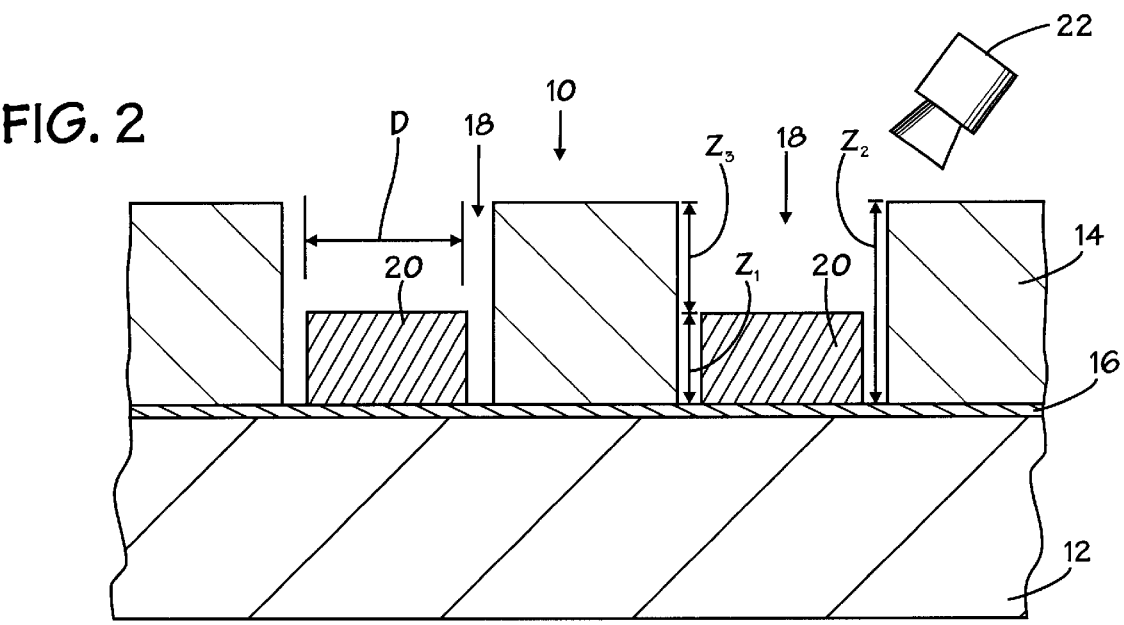
FIG. 2 is a cross-sectional of FIG. 1 taken at section 2—2 in accordance with the present invention.

In the drawings described below, reference numerals are generally repeated where identical elements appear in more than one figure. FIGS. 1 and 2 depict, respectively, a plan view and a cross-sectional view of an exemplary embodiment of a circuit device 10 that is suitable for calibrating a semiconductor workpiece inspection tool. The device 10 includes a substrate 12 upon which an insulating film 14 is formed. Another insulating film 16 may be interposed between the insulating film 14 and the substrate 12 as desired. The insulating film 14 is provided with a plurality of openings 18 in which a plurality of members or pegs 20 is formed. Each of the plurality of members 20 is fabricated with a known diameter D and a known height $Z_1$, and from a material that will provide a reflective surface and that may be resistant to etching processes to form the openings 18. The members 20 provide known targets of known geometry that provide for the accurate and rapid calibration of an inspection tool 22 that is used to inspect for defects in contact holes, such as the openings 18.

Figure 3:
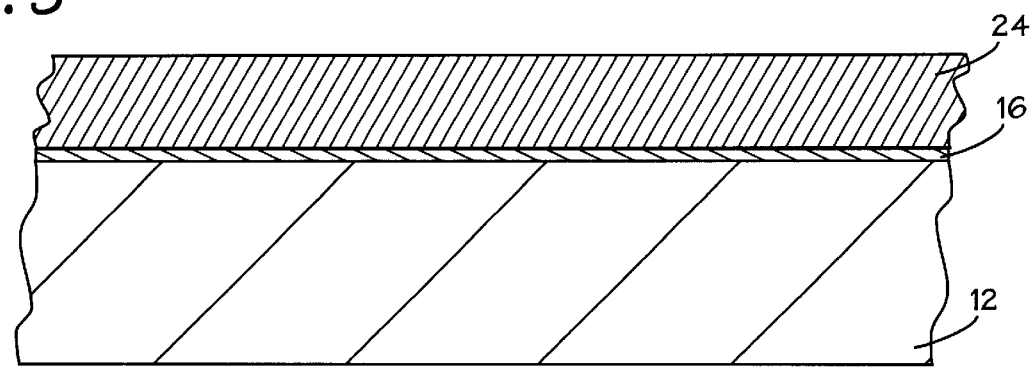
FIG. 3 is a cross-sectional view like FIG. 2 depicting the initial stages of fabrication of the circuit device of FIG. 1 in accordance with the present invention.

An exemplary process flow for fabricating the circuit device 10 in accordance with the present invention may be understood by referring now to FIGS. 3, 4, 5 and 6 and initially to FIG. 3. The insulating film 16 may be applied to the substrate 12 using well known thermal oxidation or chemical vapor deposition techniques. In an exemplary embodiment, the insulating film 16 consists of a pad oxide film of about 50 to 100 Å formed by thermal oxidation in a rapid thermal anneal process.

Next, a film 24 is blanket deposited on the insulating layer 16. Through subsequent etch definition, the film 24 will be transformed into the members 20 depicted in FIG. 2. Accordingly, the film 24 is advantageously composed of a material that presents a highly reflective upper surface and that is resistant to the etch processes used to fabricate the openings 18 in the insulating film 14. Exemplary materials include, for example, tungsten, titanium, aluminum, refractory metal silicides, laminates of these or the like. It is desirable for the material selected for the film 24 to exhibit the same types of optical properties as the materials selected to form contacts for a given integrated circuit that will be scanned by the inspection tool 22. Thus, where the contacts for an integrated circuit consist, for example, of a laminate of aluminum over titanium capped by a titanium nitride film, the film 24 will advantageously have the same composition. In an exemplary embodiment, the film 24 may have a thickness of about 10,000 to 12,000 Å and consist of the aforementioned laminate. Deposition may be by well known physical vapor deposition or chemical vapor deposition techniques.

Figure 4:
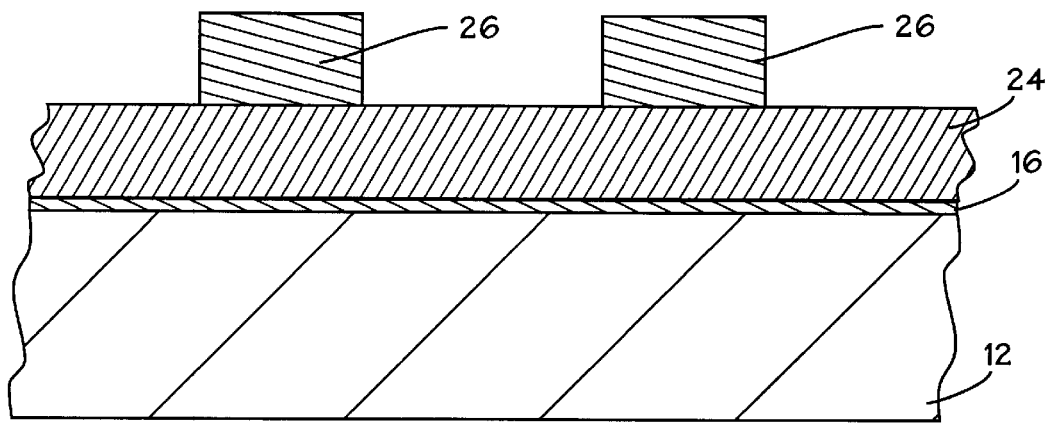
FIG. 4 is a cross-sectional view like FIG. 3 depicting intermediary stages of fabrication of the circuit device of FIG. 1 in accordance with the present invention.

Referring now to FIG. 4, mask structures 26 are patterned on the film 24 using well known photoresist application and lithographic patterning techniques. In accordance with the present invention, the mask structures 26 are patterned in size and location so that after subsequent etch of the film 24, the position and shapes of the underlying members 20 will coincide with the initial shape and position of the later formed openings 18. To this end, the mask structures 26 are patterned with the same mask or reticle (not shown) that is later used to pattern mask structures for etch definition of the openings 18 depicted in FIG. 2, but using the opposite type of resist. Thus, a negative resist is used to form the mask structures 26 while a positive type of resist is used later as described below.

Figure 5:
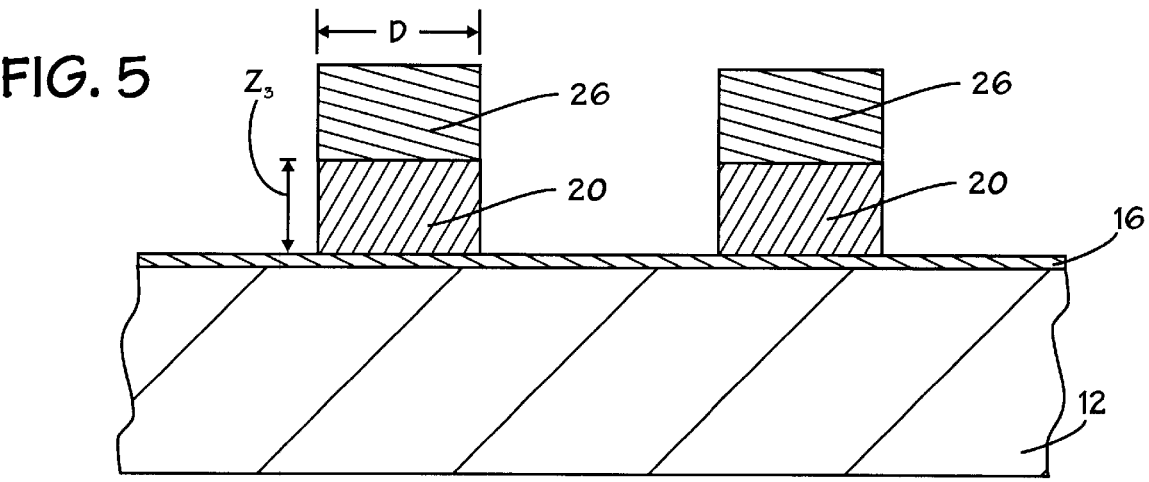
FIG. 5 is a cross-sectional view like FIG. 4 depicting intermediary stages of fabrication of the circuit device of FIG. 1 in accordance with the present invention.

Referring now to FIG. 5, the film 24 is anisotropically etched to yield the members 20. A variety of well known etch chemistries and techniques may be used to perform the etch, such as, for example, reactive ion etching, chemical plasma etching or the like and chemistries such as, for example, $BCl_3$, $Cl_2$, $N_2$, or $CF_4$ or the like. The height $Z_1$, diameter D, and the general profile of the members 20 is dictated in large part by the exposure process used to pattern the mask structures 26. For example, longer photoresist exposure times generally will result in a more robust mask structure 26 that is more resistant to the etching of the film 24 and thus more protective of the underlying members 20. In this way, sidewall and top surface attack of the members 20 will occur slightly if at all during the etch. In contrast, shorter exposure times will produce mask structures 26 that will be more easily attacked during the etching process and thus produce more sidewall and top surface attack of the underlying members 20. In this circumstance, the diameters D and the heights $Z_1$ of the underlying members 20 will be smaller than comparably sized mask structures 26 produced by a longer exposure times. In any event, the resist lithography is selected so that the members 20 will be fabricated with a known height $Z_1$ and a known diameter D.

Figure 6:
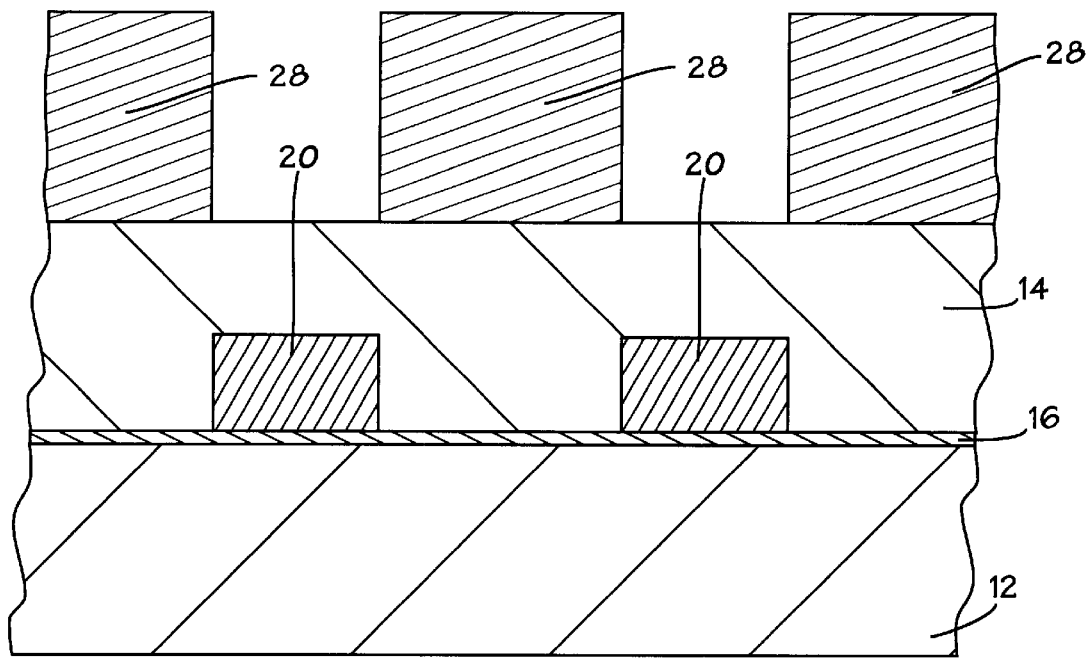
FIG. 6 is a cross-sectional view like FIG. 4 depicting intermediary stages of fabrication of the circuit device of FIG. 1 in accordance with the present invention.

Referring now to FIG. 6, the mask structures 26 are first stripped by well known ashing and solvent and/or acidic solution cleaning processes and the insulating film 14 is thereafter blanket established over the members 20. The insulating film 14 may be composed of a variety of insulating materials commonly used in semiconductor processing, such as, for example, tetra-ethyl-ortho-silicate ("TEOS"), boro-phospho-silicate-glass ("BPSG"), silicon dioxide, laminates of these or the like. In an exemplary embodiment, TEOS is applied to a depth of about 8,000 to 12,000 Å. Following the deposition of the insulating layer 14, a planarization step is performed to planarize the upper surface of the layer 14. The planarization may be by chemical mechanical polishing, etch back planarization or the like.

Next, mask structures 28 are patterned on the insulating film 14 using positive photoresist and the same reticle or mask (not shown) that was originally used to pattern the mask structures 26 depicted in FIG. 4. Note that the use of the same mask or reticle but with the opposite type of photoresist, that is, positive versus negative, produces the mask structures 28 with an inverse pattern to that of the mask structures 26 depicted in FIG. 4.

With the mask structures 28 in place, the insulating film 14 is anisotropically etched to yield the defined openings 18 with a depth $Z_2$ as depicted in FIG. 2. Again, well known anisotropic etching processes, such as, for example, reactive ion etching, chemical plasma etching or the like may be used in conjunction with etch chemistries suitable to attack oxide, such as, for example, $C_4F_8$, CO, argon, or $CHF_3$ or the like. Etch end point may be by timing. Note that the etch of the insulating film 14 is not completely anisotropic in that the openings 18 will generally have a slightly larger diameter than the known diameter D of the members 20.

Referring again to FIG. 2, with the openings 18 formed so that the members 20 are exposed, the inspection of the circuit device 10 may be performed with the inspection tool 22. The members 20 are fabricated to mimic contact defects that frequently occur in semiconductor processing. With their known geometry and highly reflective upper surfaces, the members 20 permit the inspection tool 22 to be readily focused at a depth $Z_3$ into the openings 18. The calibration of the inspection tool 22 to may now be carried out quickly and accurately using these standardized faux defects.

Figure 7:
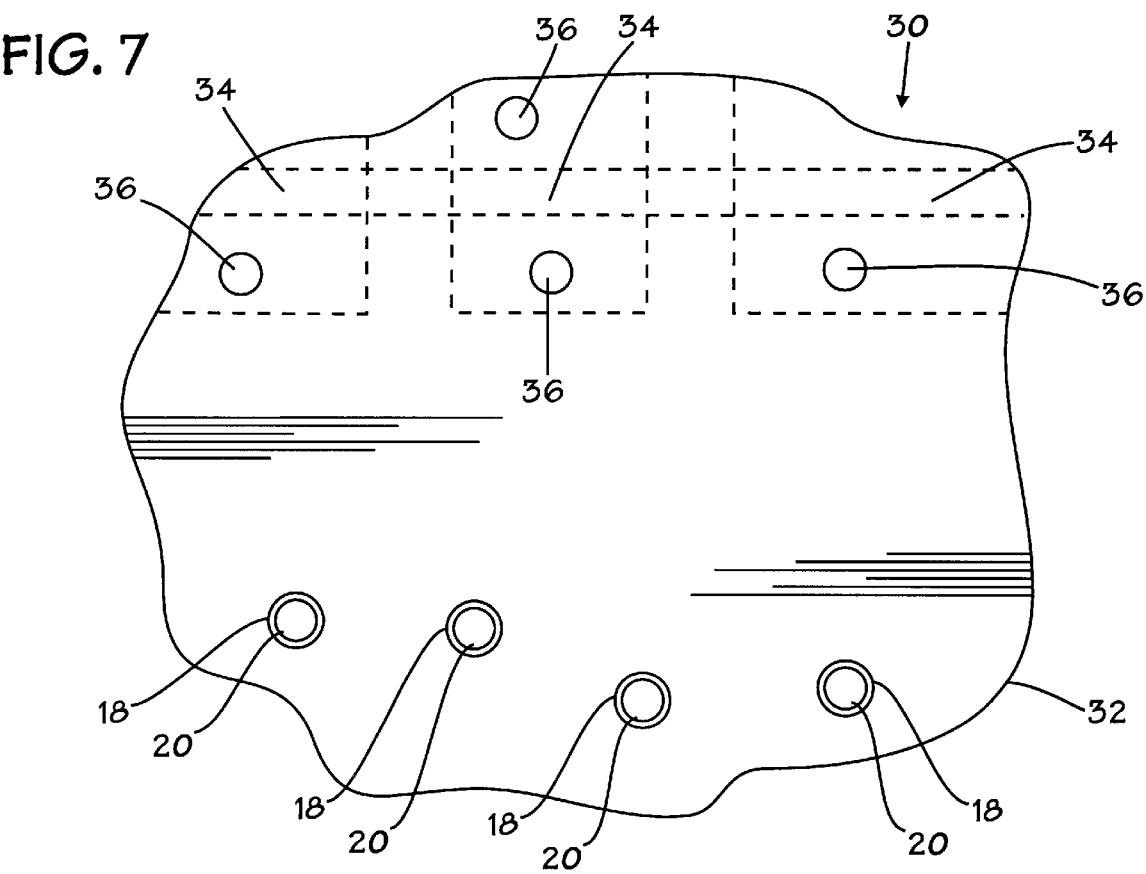
FIG. 7 is a plan view of an exemplary embodiment of an integrated circuit incorporating the circuit device of FIG. 1 in accordance with the present invention.

In the foregoing illustrated embodiment, the circuit device 10 is fabricated as a discrete test device that may be used to calibrate the inspection tool 22. However, the skilled artisan will appreciate that the members 20 and the openings 18 may be integrated into an otherwise active integrated circuit. For example, and as depicted in FIG. 7, an integrated circuit 30 may be fabricated on a substrate with a plurality of transistors 34 or other circuit devices, a plurality of active contacts 36 and a plurality of the openings 18 and the members 20. The openings 18 and the members 20 may be fabricated using the techniques described above. This incorporation of the members 20 and the openings 18 into production type integrated circuits provides for the simultaneous calibration of inspection tools and contact defect inspection without the need for separate and discrete test wafers.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A circuit device, comprising:

a substrate;

an insulating film positioned on the substrate and having a plurality of openings therein; and a plurality of members, each of the plurality of members being positioned in one of the plurality of openings and having known dimensions, the plurality of members providing a known set of defects in the plurality of openings to facilitate inspection of the plurality of openings.

2. The circuit device of claim 1, wherein the plurality of members have a reflective upper surface.

3. The circuit device of claim 1, wherein the insulating film comprises oxide.

4. The circuit device of claim 1, wherein the plurality of openings are cylindrical.

5. The circuit device of claim 4, wherein the plurality of members are cylindrical.

6. The circuit device of claim 1, wherein the plurality of members comprise metal.

7. The circuit device of claim 1, wherein the plurality of members comprise an anti-reflective coating.

8. The circuit device of claim 1, wherein a portion of the plurality of openings comprise contact holes.

9. The circuit device of claim 1, comprising a plurality of transistors.

10. A test circuit device, comprising:

a substrate;

an insulating film positioned on the substrate and having a plurality of openings therein; and a plurality of metal pegs, each of the plurality of metal pegs being positioned in one of the plurality of openings and having known dimensions, the plurality of metal pegs providing a known set of defects in the plurality of openings to facilitate inspection of the plurality of openings.

11. The test circuit device of claim 10, wherein the plurality of members have a reflective upper surface.

12. The test circuit device of claim 10, wherein the insulating film comprises oxide.

13. The test circuit device of claim 10, wherein the plurality of openings are cylindrical.

14. The test circuit device of claim 13, wherein the plurality of metal pegs are cylindrical.

15. The test circuit device of claim 10, wherein the metal comprises a titanium-aluminum laminate.

16. The test circuit device of claim 10, wherein the plurality of members comprise an anti-reflective coating.

17. The test circuit device of claim 16, wherein the anti-reflective coating comprises titanium nitride.

* * * * *